US007008953B2

(12) United States Patent
Kephart et al.

(10) Patent No.: US 7,008,953 B2
(45) Date of Patent: Mar. 7, 2006

(54) 3, 5 DISUBSTITUTED INDAZOLE COMPOUNDS, PHARMACEUTICAL COMPOSITIONS, AND METHODS FOR MEDIATING OR INHIBITING CELL PROLIFERATION

(75) Inventors: Susan Elizabeth Kephart, San Diego, CA (US); Indrawan James McAlpine, San Diego, CA (US); Siegfried Heinz Reich, Solana Beach, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 11 days.

(21) Appl. No.: 10/866,059

(22) Filed: Jun. 10, 2004

(65) Prior Publication Data

US 2005/0026960 A1    Feb. 3, 2005

Related U.S. Application Data

(60) Provisional application No. 60/491,474, filed on Jul. 30, 2003, provisional application No. 60/492,073, filed on Jul. 31, 2003.

(51) Int. Cl.
*A61K 31/4439* (2006.01)
*C07D 401/14* (2006.01)

(52) U.S. Cl. .................................. 514/339; 546/273.4
(58) Field of Classification Search ............. 546/273.4; 514/339
See application file for complete search history.

(56) References Cited

U.S. PATENT DOCUMENTS

| 4,051,145 A | 9/1977 | Dupre et al. |
| 4,415,569 A | 11/1983 | Yasuo et al. |
| 4,978,603 A | 12/1990 | Inoue et al. |
| 5,208,248 A | 5/1993 | Baker et al. |
| 6,555,539 B1 | 4/2003 | Reich et al. |

FOREIGN PATENT DOCUMENTS

| EP | 0 023 633 | 2/1981 |
| EP | 0 518 805 A1 | 2/1992 |
| EP | 0 494 774 A1 | 7/1992 |
| EP | 0 780 386 B1 | 6/1997 |
| EP | 0 818 442 A2 | 1/1998 |
| EP | 0 904 769 B1 | 3/1999 |
| FR | 2 831 536 | 5/2003 |
| GB | 1 376 600 | 12/1974 |
| GB | 2 345 486 A | 7/2000 |
| JP | 59 228248 | 12/1984 |
| JP | 60 4184 | 1/1985 |
| WO | WO 96/20192 | 7/1996 |
| WO | WO 98/02438 | 1/1998 |
| WO | WO 98/43969 | 10/1998 |
| WO | WO 00/38786 | 7/2000 |
| WO | WO 01/53268 A2 | 7/2001 |
| WO | WO 01/85726 | 11/2001 |
| WO | WO 02/10137 | 2/2002 |
| WO | WO 03/004488 | 1/2003 |
| WO | WO 03/035644 A1 | 5/2003 |

OTHER PUBLICATIONS

Davies, S., et al., "Specificity and Mechanism of Action of Some Commonly Used Protein Kinase Inhibitors," *Biochemical Journal*, 2000, 95-105, vol. 351.
De Lucca, G., et al., "Stereospecific Synthesis, Structure—Activity Relationship, and Oral Bioavailability of Tetrahydropyrimidin-2-one HIV Protease Inhibitors," *Journal of Medicinal Chemistry*, 1999, 135-152, vol. 42, No. 1.
Fujimura, Y., et al., "Synthesis and Pharmacological Activities of 3-Phenylindazole Derivatives," *Yakugaku Zasshi*, 1986, 995-1001, vol. 106, No. 11.
Fujimura, Y., et al., "Synthesis and Pharmacological Activities of 2,3-Dihydro-1*H*-pyrazolo[1,2-a]indazolium Derivatives," *Yakugaku Zasshi*, 1986, 1002-1007, vol. 106, No. 11.
Hosoi, T., et al., "Evidence for cdk5 as a Major Activity Phosphorylating Tau Protein in Porcine Brain Extract," *Journal of Biochemistry*, 1995, 741-749, vol. 117, No. 4.
Jeffrey, P., et al., "Mechanism of CDK Activation Revealed by the Structure of a CyclinA-CDK2 Complex," *Nature*, 1995, 313-320, vol. 376, No. 6538.
Meijer, L., et al., "Chemical Inhibitors of Cyclin-Dependent Kinases," *Methods in Enzymology*, 1997, 113-128, vol. 283.
Mosmann, T., "Rapid Colorimetric Assay for Cellular Growth and Survival: Application to Proliferation and Cytotoxicity Assays," *Journal of Immunological Methods*, 1983, 55-63, vol. 65.
Rosenblatt, J., et al., "Purification and Crystallization of Human Cyclin-Dependent Kinase 2," *Journal of Molecular Biology*, 1993, 1317-1319, vol. 230.
Schang, L. et al., Roscovitine, a Specific Inhibitor of Cellular Cyclin-Dependent Kinases, Inhibits Herpes Simplex Virus DNA Synthesis in the Presen.
Sun, J., et al., "Efficient Synthesis of 5-(Bromomethyl)-and 5-(Aminomethyl)-1-THP-Indazole," *Journal of Organic Chemistry*, 1997, 5627-5629, vol. 62, No. 16.
Wentrup, C., et al., "Intramolecular Cyclization of Nitrile Imines. Synthesis of Indazoles, Fluorenes, and Aza Analogues," *Journal of Organic Chemistry*, 1978, 2037-2041, vol. 43, No. 10.

*Primary Examiner*—Patricia L. Morris
(74) *Attorney, Agent, or Firm*—Bryan C. Zielinski; Wendy L. Hsu

(57) ABSTRACT

3,5 disubstituted indazole compounds that modulate and/or inhibit cell proliferation, such as the activity of protein kinases are described. These compounds and pharmaceutical compositions containing them are capable of mediating CDK dependent diseases to modulate and/or inhibit unwanted cell proliferation. The invention is also directed to the therapeutic or prophylactic use of pharmaceutical compositions containing such compounds, and to methods of treating cancer as well as other disease states associated with unwanted angiogenesis and/or cellular proliferation, such as diabetic retinopathy, neovascular glaucoma, rheumatoid arthritis, and psoriasis, by administering effective amounts of such compounds.

4 Claims, No Drawings

3, 5 DISUBSTITUTED INDAZOLE COMPOUNDS, PHARMACEUTICAL COMPOSITIONS, AND METHODS FOR MEDIATING OR INHIBITING CELL PROLIFERATION

This application claims the benefit of U.S. Provisional Application No. 60/491,474 filed Jul. 30, 2003, and U.S. Provisional Application No. 60/492,073 filed Jul. 31, 2003, the contents of which are hereby incorporated by reference in their entireties.

FIELD OF THE INVENTION

This invention is directed to 3,5 disubstituted indazoles with substituted benzamidazoles in the 3-position which mediate and/or inhibit cell proliferation through the activity of protein kinases, particularly through mediation of cyclin dependent kinases such as CDK1, CDK2, CDK4, and CDK6. The invention is further related to pharmaceutical compositions containing such compounds and compositions, and to methods of treating cancer as well as other disease states associated with unwanted angiogenesis and/or cellular proliferation, by administering effective amounts of such compounds.

BACKGROUND OF THE INVENTION

Cell proliferation occurs in response to various stimuli and may stem from de-regulation of the cell division cycle (or cell cycle), the process by which cells multiply and divide. Hyperproliferative disease states, including cancer, are characterized by cells rampantly winding through the cell cycle with uncontrolled vigor due to, for example, damage to the genes that directly or indirectly regulate progression through the cycle. Thus, agents that modulate the cell cycle, and thus hyperproliferation, could be used to treat various disease states associated with uncontrolled or unwanted cell proliferation.

Mechanisms of cell proliferation are under active investigation at cellular and molecular levels. At the cellular level, de-regulation of signaling pathways, loss of cell cycle controls, unbridled angiogenesis or stimulation of inflammatory pathways are under scrutiny, while at the molecular level, these processes are modulated by various proteins, among which protein kinases are prominent suspects. Overall abatement of proliferation may also result from programmed cell death, or apoptosis, which is also regulated via multiple pathways, some involving proteolytic enzyme proteins. Among the candidate regulatory proteins, protein kinases are a family of enzymes that catalyze phosphorylation of the hydroxyl group of specific tyrosine, serine or threonine residues in proteins. Typically, such phosphorylation dramatically perturbs the function of the protein, and thus protein kinases are pivotal in the regulation of a wide variety of cellular processes. For example, without wishing to be bound to a particular theory, it is believed that as inhibitors of protein kinases, such as, for example, cyclin dependent kinases ("CDK"), the inventive agents can modulate the level of cellular RNA and DNA synthesis and therefore are expected to be useful in the treatment of viral infections such as HIV, human papilloma virus, herpesvirus, Epstein-Barr virus, adenovirus, Sindbis virus, poxvirus and the like. (See Schang, et al, *J. Virol.* 74, 2107–2120 (2000)). Additionally, CDK5 has been implicated in the phosphorylation of tau protein, suggesting potential methods of treating or preventing Alzheimer's disease (Hosoi, et al, *J. Biochem.* (*Tokyo*), 117, 741–749 (1995)). CDKs are serine-threonine protein kinases that play critical roles in regulating the transitions between different phases of the cell-cycle, such as the progression from a quiescent stage in $G_1$ (the gap between mitosis and the onset of DNA replication for a new round of cell division) to S (the period of active DNA synthesis), or the progression from $G_2$ to M phase, in which active mitosis and cell-division occurs. CDK complexes are formed through association of a regulatory cyclin subunit (e.g., cyclin A, B1, B2, D1, D2, D3, and E) and a catalytic kinase subunit (e.g., CDK1, CDK2, CDK4, CDK5, and CDK6). As the name implies, the CDKs display an absolute dependence on the cyclin subunit in order to phosphorylate their target substrates, and different kinase/cyclin pairs function to regulate progression through specific phases of the cell-cycle.

A number of indazole derivatives have thus far been identified to have therapeutic potential: GB 2345486 discloses indazole derivatives as tyrosine kinase inhibitors, EP0518805 identifies indazoles substituted with piperidines having sigma receptor activity; WO 89/43969 discloses indazoles of cyclic ureas useful as HIV protease inhibitors; U.S. Pat. No. 4,415,569 identifies pyrazoloindazole derivatives having bronchodilating action; U.S. Pat. No. 5,208,248 discloses indazoles for the treatment of migraines. Other therapeutic applications for indazole derivatives are discussed in WO 96/20192, EP 04994774, JP 60/004184, EP0023633, U.S. Pat. No. 4,051,145, JP59/228248, GB 1/376600, U.S. Pat. No. 4,978,603, EP0904769 and in the literature by De Lucca et al, *Journal of Medicinal Chemistry*, 42, 135–52 (1999). General synthetic schemes for the preparation of indazole derivatives are disclosed Wentrup et al, *Journal of Organic Chemistry*, 43, 203–741(1978); Fugimura et al, *Chemical Abbstracts*, 1070, 749 (1987). More particularly, 3,5 substituted indazoles have been identified as protein kinase inhibitors: WIPO International Publication No. 01/85726 discloses indazole compounds substituted with 1,1-dioxoisothiazolidine as CDK inhibitors; WO 02/10137 discloses 3,5 substituted indazoles as inhibitors of Jun N-terminal kinase inhibitors; and U.S. Pat. No. 6,555,539 and WO 03/004488 discloses 3,5 substituted indazoles with a benzimidazole in the 3-position.

There is still a need, however, for more potent inhibitors of CDK and in particular, for CDK inhibitors which possess both high affinity for the target CDK kinase as well as high selectivity versus other protein kinases. The inventive compounds are generally more selective for CDK inhibitors than the compounds described in previous publications.

SUMMARY OF THE INVENTION

An object of the invention is to provide potent and selective inhibitors of CDK. Accordingly, one object of the invention is to attain compounds and drug compositions that inhibit CDK activity, or cyclin complexes thereof. A further object is to provide an effective method of treating cancer indications through CDK inhibition. Another object is to achieve pharmaceutical compositions containing compounds effective to block the transition of cancer cells into their proliferative phase. These and other objects and advantages of the invention, which will become apparent in light of the detailed description below, are achieved through use of cell-cycle control agents of the invention described below.

According to these objectives, there is provided in accordance with the present invention a compound or a pharmaceutically acceptable salt or solvate of the Formula I:

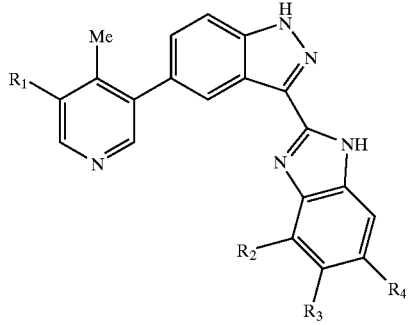

I wherein $R^1$, $R^2$, $R^3$ and $R^4$ are selected from the group consisting of H, halo, cyano, nitro, trifluoromethoxy, trifluoromethyl, azido, hydroxy, $C_{1-C6}$ alkoxy, $C_{1-C10}$ alkyl, $C_{2-C6}$ alkenyl, $C_{2-C6}$ alkynyl, —C(O)$R^5$, —C(O)O$R^5$, —OC(O)$R^5$, —N$R^5$C(O)$R^6$, —C(O)N$R^5R^6$, —(C$R^5R^6$)N$R^7R^8$, —C$R^5R^6$N$R^7R^8$, —N$R^5$O$R^6$, —SO$_2$N$R^5R^6$, —S(O)$_j$(C$_{1-C6}$ alkyl) wherein j is an integer from 0 to 2, —(C$R^5R^6$)$_t$(C$_{6-C10}$ aryl), —(C$R^5R^6$)$_t$(C$_{3-C10}$ cycloalkyl), —(C$R^5R^6$)$_t$(4–10 membered heterocyclic), —(C$R^5R^6$)$_q$C(O)(C$R^7R^8$)$_t$(C$_{6-C10}$ aryl), —(C$R^5R^6$)$_q$C(O)(C$R^7R^8$)$_t$(C$_{3-C10}$ cycloalkyl), —(C$R^5R^6$)$_q$C(O)(C$R^7R^8$)$_t$(4–10 membered heterocyclic), —(C$R_5R^6$)$_q$O(C$R^7R^8$)$_q$(C$_{6-C10}$ aryl), —(C$R_5R^6$)$_q$O(C$R^7R^8$)$_q$(C$_3C_{10}$ cycloalkyl), —(C$R^5R^6$)$_q$O(C$R^7R^8$)$_q$(4–10 membered heterocyclic), —(C$R^5R^6$)$_q$SO$_2$(C$R^7R^8$)$_t$(C$_{6-C10}$ aryl), —(C$R_5R^6$)$_q$SO$_2$(C$R^7R^8$)$_t$(C$_{3-C10}$ cycloalkyl) and —(C$R^5R^6$)$_q$SO$_2$(C$R^7R^8$)$_t$(4–10 membered heterocyclic), wherein q and t are each independently an integer from 0 to 5, 1 or 2 ring carbon atoms of the cycloalkyl or heterocyclic moieties of the foregoing $R^1$, $R^2$, $R^3$ or $R^4$ groups are optionally substituted with an oxo (=O) moiety, each $R^5$, $R^6$, $R^7$ and $R^8$ is independently selected from H, $C_{1-C6}$ alkyl; and, wherein $R^1$, $R^2$, $R^3$ and $R^4$ are not H at the same time.

In one embodiment $R^1$ is —(C$R^5R^6$)N$R^7R^8$, and $R^2$, $R^3$ and $R^4$ are independently selected from H or F.

In one embodiment $R^1$ is ethylaminomethyl, $R^3$ is H, and $R^2$ and $R^4$ are F.

In another embodiment $R^1$ is ethylaminomethyl, $R^2$ and $R^4$ are H, and $R^3$ is F.

In a further embodiment, the present invention is directed to a compound selected from

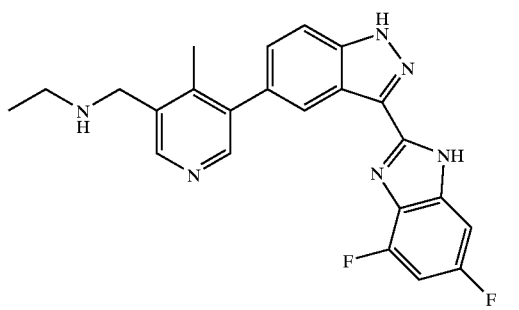

or

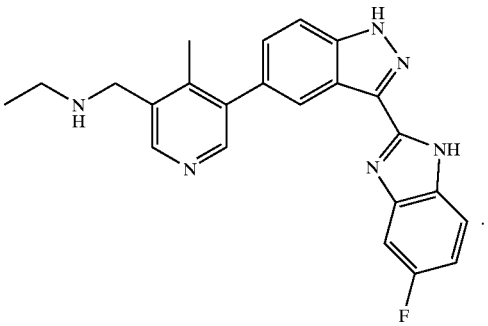

The invention also provides methods for making compounds of Formula I.

There is further provided in accordance with the invention, a method of using a compound as a cell-cycle control agent for treating a disease or disorder mediated by inhibition of kinase comprising administering to a patient in need thereof, a compound of Formula, I or a pharmaceutically acceptable salt or solvate of a compound of the Formula I.

The invention further provides a method of treating mycotic infection, malignancies or cancer as well as other disease states associated with unwanted angiogenesis and/or cellular proliferation, comprising administering effective amounts of a compound of Formula I or a pharmaceutically acceptable salt or solvate of a compound of the Formula I to a patient in need of such treatment.

The invention also provides a method of selectively inhibiting CDK kinase activity by administering a compound of the Formula I or a pharmaceutically acceptable salt or solvate of a compound of the Formula I to a patient in need thereof.

There is also provided in accordance with the invention, a pharmaceutical composition containing a compound of the Formula I or a pharmaceutically acceptable salt or solvate of a compound of the Formula I, and the therapeutic use of the composition in treating diseases mediated by kinase activity, such as cancer, as well as other disease states associated with unwanted angiogenesis and/or cellular proliferation, such as diabetic retinopathy, neovascular glaucoma, rheumatoid arthritis, and psoriasis.

The inventive agents and compositions containing such agents may be useful in treating various disorders or disease states associated with uncontrolled or unwanted cellular proliferation, such as cancer, autoimmune disorders, viral diseases, fungal diseases, neurodegenerative disorders, and cardiovascular diseases. Thus, the invention is also directed to methods of treating such diseases by administering an effective amount of the inventive agent.

Other aspects, advantages, and features of the invention will become apparent from the detailed description below.

The compounds and compositions of the present invention, are useful as anti-proliferative agents and as inhibitors of mammalian kinase complexes, insect kinase or fungal kinase complexes. For example, CDK complexes can be inhibited. Such compounds and compositions are also useful for controlling proliferation, differentiation, and/or apoptosis.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight or branched moieties. A "$C_{1-C6}$ alkyl" indicates a straight or branched alkyl moiety having 1 to 6 carbon atoms, and so forth.

The term "alkenyl" refers to a straight- or branched-chain alkenyl group having 2 to 12 carbon atoms in the chain. Illustrative alkenyl groups include prop-2-enyl, but-2-enyl, but-3-enyl, 2-methylprop-2-2nyl, hex-2-2nyl, ethenyl, pentenyl, and the like.

The term "alkynyl" refers to a straight- or branched-chain alkynyl group having from 2 to 12 carbon atoms in the chain. Illustrative alkynyl groups include prop-2-ynyl, but-2-ynyl, but-3-ynyl, 2-methylbut-2-ynyl, hex-2-ynyl, ethynyl, propynyl, pentynyl and the like.

The term "cycloalkyl" refers to a saturated or partially saturated, monocyclic or fused or spiro polycyclic, carbocycle having from three to twelve ring atoms per ring. Illustrative examples of cycloalkyl groups include the following moieties:

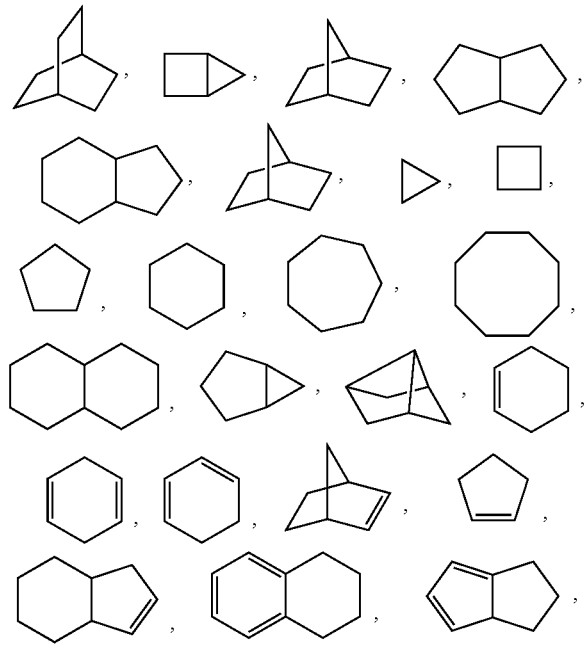

and the like.

The term "aryl", as used herein, unless otherwise indicated, includes an organic radical derived from an aromatic hydrocarbon by removal of one hydrogen, such as phenyl or naphthyl.

The term "4–10 membered heterocyclic", as used herein, unless otherwise indicated, includes aromatic and non-aromatic heterocyclic groups containing one to four heteroatoms each selected from O, S and N, wherein each heterocyclic group has from 4–10 atoms in its ring system, and with the proviso that the ring of said group does not contain two adjacent O or S atoms. Non-aromatic heterocyclic groups include groups having only 4 atoms in their ring system, but aromatic heterocyclic groups must have at least 5 atoms in their ring system. The heterocyclic groups include benzo-fused ring systems. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperdino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). The 4–10 membered heterocyclic may be optionally substituted on any ring carbon, sulfur, or nitrogen atom(s) by one to two oxo, per ring. An example of a heterocyclic group wherein 2 ring carbon atoms are substituted with oxo moieties is 1,1-dioxo-thiomorpholinyl. Other Illustrative examples of 4–10 membered heterocyclic are derived from, but not limited to, the following:

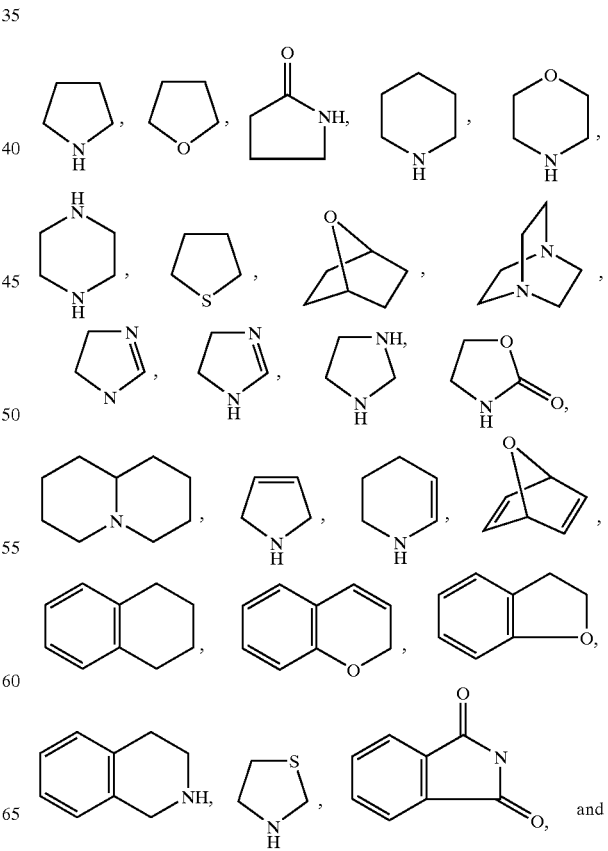

-continued

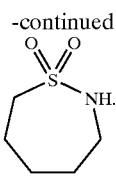

Unless otherwise indicated, the term "oxo" refers to =O.

The term "amide" refers to the radical —C(O)N(R')(R") where R' and R" are each independently selected from hydrogen, alkyl, alkenyl, alkynyl, —OH, alkoxy, cycloalkyl, heterocycloalkyl, heteroaryl, aryl as defined above; or R' and R" cyclize together with the nitrogen to form a heterocycloalkyl or heteroaryl as defined above.

The term "substituted" means that the specified group or moiety bears one or more substituents. The term "unsubstituted" means that the specified group bears no substituents.

Within the invention it is understood that a compound of Formula I may exhibit the phenomenon of tautomerism and that the formula drawings within this specification represent only one of the possible tautomeric forms. It is to be understood that the invention encompasses any tautomeric form which modulates and/or inhibits kinase activity and is not to be limited merely to any one tautomeric form utilized within the formula drawings.

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, Formulas I and II are intended to cover solvated as well as unsolvated forms of the identified structures. For example, Formulas I and II include compounds of the indicated structure in both hydrated and non-hydrated forms. Other examples of solvates include the structures in combination with isopropanol, ethanol, methanol, DMSO, ethyl acetate, acetic acid, or ethanolamine.

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrovic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

Cell-cycle control agents in accordance with the invention are useful as pharmaceuticals for treating proliferative disorders in mammals, especially humans, marked by unwanted proliferation of endogenous tissue. Compounds of the Formula I may be used for treating subjects having a disorder associated with excessive cell proliferation, e.g., cancers, psoriasis, immunological disorders involving undesired proliferation of leukocytes, and restenosis and other smooth-muscle disorders. Furthermore, such compounds may be used to prevent de-differentiation of postmitotic tissue and/or cells.

Diseases or disorders associated with uncontrolled or abnormal cellular proliferation include, but are not limited to, the following:

a variety of cancers, including, but not limited to, carcinoma, hematopoietic tumors of lymphoid lineage, hematopoietic tumors of myeloid lineage, tumors of mesenchymal origin, tumors of the central and peripheral nervous system and other tumors including melanoma, seminoma and Kaposi's sarcoma and the like.

a disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

defective apoptosis-associated conditions, such as cancers (including but not limited to those types mentioned hereinabove), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus erythematosus, rheumatoid arthritis, psoriasis, autoimmune mediated glomerulonephritis, inflammatory bowel disease and autoimmune diabetes mellitus), neurodegenerative disorders (including but not limited to Alzheimer's disease, amyotrophic lateral sclerosis, retinitis pigmentosa, Parkinson's disease, AIDS-related dementia, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteroporosis and arthritis), aspirin-sensitive rhinosinusitis, cystic fibrosis, multiple sclerosis, kidney diseases and cancer pain.

The active agents of the invention may also be useful in the inhibition of the development of invasive cancer, tumor angiogenesis and metastasis.

Moreover, the active agents of the invention, for example, as inhibitors of the CDKs, can modulate the level of cellular RNA and DNA synthesis and therefore are expected to be useful in the treatment of viral infections such as HIV, human papilloma virus, herpesvirus, Epstein-Barr virus, adenovirus, Sindbis virus, poxvirus and the like.

Compounds and compositions of the invention inhibit the kinase activity of, for example, CDK/cyclin complexes, such as those active in the $G_0$ or $G_1$ stage of the cell cycle, e.g., CDK2, CDK4, and/or CDK6 complexes.

The specific dosage amount of a cell-cycle control agent being administered to obtain therapeutic or inhibitory effects may be determined in a manner known in the art according to the particular circumstances surrounding the case, including, e.g., the specific agent being administered, the route of administration, the condition being treated, and the subject or host being treated. An exemplary total daily dose of a cell-cycle control agent, which may be administered in single or multiple doses, contains a dosage level of from about 0.01 mg/kg body weight to about 50 mg/kg body weight.

The cell-cycle control agents of the invention may be administered by any of a variety of suitable routes, such as orally, rectally, transdermally, subcutaneously, intravenously, intramuscularly, or intranasally. The cell-cycle control agents are preferably formulated into compositions suitable for the desired routes before being administered.

A pharmaceutical composition or preparation according to the invention comprises an effective amount of a cell-cycle control agent, optionally one or more other active agents, and a pharmaceutically acceptable carrier, such as a diluent or excipient for the agent; when the carder serves as a diluent, it may be a solid, semi-solid, or liquid material acting as a vehicle, excipient, or medium for the active ingredient(s). Compositions according to the invention may be made by admixing the active ingredient(s) with a carrier, or diluting it with a carrier, or enclosing or encapsulating it within a carrier, which may be in the form of a capsule, sachet, paper container, or the like. Exemplary ingredients, in addition to one or more cell-cycle control agents and any other active ingredients, include Avicel (microcrystalline cellulose), starch, lactose, calcium sulfate dihydrate, terra alba, sucrose, talc, gelatin, agar, pectin, acacia, magnesium stearate, stearic acid, peanut oil, olive oil, glyceryl monostearate, Tween 80 (polysorbate 80), 1,3-butanediol, cocoa butter, beeswax, polyethylene glycol, propylene glycol, sorbitan monostearate, polysorbate 60, 2-octyldodecanol, benzyl alcohol, glycine, sorbic acid, potassium sorbate, disodium hydrogen phosphate, sodium chloride, and water.

The compositions may be prepared in any of a variety of forms suitable for the desired mode of administration. For example, pharmaceutical compositions may be prepared in the form of tablets, pills, powders, lozenges, sachets, cachets, elixirs, suspensions, emulsions, solutions, syrups, aerosols (as solids or in liquid media), ointments (e.g., containing up to 10% by weight of a cell-cycle control agent), soft-gel and hard-gel capsules, suppositories, sterile injectable solutions, sterile packaged powders, and the like.

Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation can be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, gylcerin and the like in concentrations ranging from 0–60% of the total volume. A compound of Formula I may be dissolved in DMSO and diluted with water. The composition may also be in the form of a solution of a salt form of the active ingredient in an appropriate aqueous vehicle such as water or isotonic saline or dextrose solution.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, hydroxypropylmethyl-cellulose, sodium carboxymethylcellulose, methyl cellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

For administration to the eye, the active agent is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/ciliary, lens, choroid/retina and sclera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

The compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

A pharmaceutical composition according to the invention comprises a cell-cycle control agent and, optionally, one or more other active ingredients, such as a known antiproliferative agent that is compatible with the cell-cycle control agent and suitable for the indication being treated.

The compounds are useful as anti-angiogenesis agents and as agents for modulating and/or inhibiting the activity of protein kinases, thus providing treatments for cancer or other diseases associated with cellular proliferation mediated by protein kinases.

Therapeutically effective amounts of the agents of the invention may be used to treat diseases mediated by modulation or regulation of protein kinases. An "effective amount" is intended to mean that amount of an agent that, when administered to a mammal in need of such treatment, is sufficient to effect treatment for a disease mediated by the activity of one or more kinases. Thus, e.g., a therapeutically effective amount of a compound of the Formula I, salt, active metabolite or prodrug thereof is a quantity sufficient to modulate, regulate, or inhibit the activity of one or more kinases such that a disease condition which is mediated by that activity is reduced or alleviated.

"Treating" is intended to mean at least the mitigation of a disease condition in a mammal, such as a human, that is affected, at least in part, by the activity of one or more kinases, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

In a specific embodiment of any of the inventive methods described herein, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restinosis.

In further specific embodiments of any of the inventive methods described herein, the method further comprises administering to the mammal an amount of one or more substances selected from anti-tumor agents, anti-angiogenesis agents, signal transduction inhibitors, and antiproliferative agents, which amounts are together effective in treating said abnormal cell growth. The compounds of the present invention may be combined with other anti-tumor agents, the methods of which are disclosed in WO038716, WO038717, WO038715, WO038730, WO038718, WO038665, WO037107, WO038786, WO038719, the contents of which are herein incorporated by reference in their entireties. Examples of anti-tumor agents include mitotic inhibitors, for example vinca alkaloid derivatives such as vinblastine vinorelbine, vindescine and vincristine; colchines allochochine, halichondrine, N-benzoyltrimethylmethyl ether colchicinic acid, dolastatin 10, maystansine, rhizoxine, taxanes such as taxol (paclitaxel), docetaxel (Taxotere), 2'-N-[3-(dimethylamino)propyl]glutaramate (taxol derivative), thiocholchicine, trityl cysteine, teniposide, methotrexate, azathioprine, fluorouricil, cytocine arabinoside, 2'2'-difluorodeoxycytidine (gemcitabine), adriamycin and mitamycin. Alkylating agents, for example cisplatin, carboplatin oxiplatin, iproplatin, Ethyl ester of N-acetyl-DL-sarcosyl-L-leucine (Asaley or Asalex), 1,4-cyclohexadiene-1,4-dicarbamic acid, 2,5-bis(1-azirdinyl)-3, 6-dioxo-, diethyl ester (diaziquone), 1,4-bis(methanesulfonyloxy)butane (bisulfan or leucosulfan) chlorozotocin, clomesone, cyanomorpholinodoxorubicin, cyclodisone, dianhydroglactitol, fluorodopan, hepsulfam, mitomycin C, hycantheonemitomycin C, mitozolamide, 1-(2-chloroethyl)-4-(3-chloropropyl)-piperazine dihydrochloride, piperazinedione, pipobroman, porfiromycin, spirohydantoin mustard, teroxirone, tetraplatin, thiotepa, triethylenemelamine, uracil nitrogen mustard, bis(3-mesyloxypropyl)amine hydrochloride, mitomycin, nitrosoureas agents such as cyclohexyl-chloroethylnitrosourea, methylcyclohexyl-chloroethylnitrosourea 1-(2-chloroethyl)-3-(2,6-dioxo-3-piperidyl)-1-nitroso-urea, bis(2-chloroethyl)nitrosourea, procarbazine, dacarbazine, nitrogen mustard-related compounds such as mechloroethamine, cyclophosphamide, ifosamide, melphalan, chlorambucil, estramustine sodium phosphate, strptozoin, and temozolamide. DNA anti-metabolites, for example 5-fluorouracil, cytosine arabinoside, hydroxyurea, 2-[(3hydroxy-2-pyrinodinyl)methylene]-hydrazinecarbothioamide, deoxyfluorouridine, 5-hydroxy-2-formylpyridine thiosemicarbazone, alpha-2'-deoxy-6-thioguanosine, aphidicolin glycinate, 5-azadeoxycytidine, beta-thioguanine deoxyriboside, cyclocytidine, guanazole, inosine glycodialdehyde, macbecin II, pyrazolimidazole, cladribine, pentostatin, thioguanine, mercaptopurine, bleomycin, 2-chlorodeoxyadenosine, inhibitors of thymidylate synthase such as raltitrexed and pemetrexed disodium, clofarabine, floxuridine and fludarabine. DNA/RNA antimetabolites, for example, L-alanosine, 5-azacytidine, acivicin, aminopterin and derivatives thereof such as N-[2-chloro-5-[[(2,4-diamino-5-methyl-6-quinazolinyl)methyl]amino] benzoyl]-L-aspartic acid, N-[4-[[(2,4-diamino-5-ethyl-6-quinazolinyl)methyl]amino]benzoyl]-L-aspartic acid, N-[2- chloro-4-[[(2,4-diaminopteridinyl)methyl]amino]benzoyl]-L-aspartic acid, soluble Baker's antifol, dichloroallyl lawsone, brequinar, ftoraf, dihydro-5-azacytidine, methotrexate, N-(phosphonoacetyl)-L-aspartic acid tetrasodium salt, pyrazofuran, trimetrexate, plicamycin, actinomycin D, cryptophycin, and analogs such as cryptophycin-52 or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; proteins, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

Anti-angiogenesis agents include MMP-2 (matrix-metalloprotienase 2) inhibitors, MMP-9 (matrix-metalloprotienase 9) inhibitors, and COX-II (cyclooxygenase 11) inhibitors. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Examples of signal transduction inhibitors include agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.). VEGF inhibitors, for example SU-5416 and SU-6668 (Sugen Inc. of South San Francisco, Calif., USA), can also be combined or co-administered with a compound of formula 1. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with a compound of formula 1. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety.

Other antiproliferative agents that may be used include inhibitors of the enzyme farnesyl protein transferase and inhibitors of the receptor tyrosine kinase PDGFr, including the compounds disclosed and claimed in the following U.S. patent application Ser. No. 09/221,946 (filed Dec. 28, 1998); Ser. No. 09/454,058 (filed Dec. 2, 1999); Ser. No. 09/501,163 (filed Feb. 9, 2000); Ser. No. 09/539,930 (filed Mar. 31, 2000); Ser. No. 09/202,796 (filed May 22, 1997); Ser. No. 09/384,339 (filed Aug. 26, 1999); and Ser. No. 09/383,755 (filed Aug. 26, 1999); and the compounds disclosed and claimed in the following U.S. provisional patent applications: 60/168,207 (filed Nov. 30,1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety.

The compound of formula 1 may also be used with other agents useful in treating abnormal cell growth or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors. Specific CTLA4 antibodies that can be used in the present invention include those described in U.S. Provisional Application 60/113,647 (filed Dec. 23, 1998) which is herein incorporated by reference in its entirety.

DETAILED DESCRIPTION AND PREFERRED EMBODIMENTS OF THE INVENTION

The inventive agents may be prepared using the reaction routes and synthesis schemes as described below, employing the techniques available in the art using starting materials that are readily available.

The preparation of specific preferred compounds of the invention is described in detail in the following examples. The artisan will recognize that the chemical reactions described may be readily adapted to prepare a number of other kinase inhibitors of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius and all parts and percentages are by weight. Reagents were purchased from commercial suppliers such as Aldrich Chemical Company or Lancaster Synthesis Ltd. and were used without further purification unless otherwise indicated. Tetrahydrofuran (THF) distilled from calcium hydride and N,N-dimethylformamide (DMF) were purchased from Aldrich in Sure seal bottles and used as received. All solvents were purified using standard methods readily known to those skilled in the art, unless otherwise indicated.

The reactions set forth below were done generally under a positive pressure of argon or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed on glass-backed silica gel 60 F 254 plates Analtech (0.25 mm) and eluted with the appropriate solvent ratios (v/v), and are denoted where appropriate. The reactions were assayed by TLC and terminated as judged by the consumption of starting material.

Visualization of the TLC plates was done with a p-anisaldehyde spray reagent or phosphomolybdic acid reagent (Aldrich Chemical 20 wt % in ethanol) and activated with heat. Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ or $MgSO_4$ prior to filtration and evaporation of the solvents under reduced pressure on a rotary evaporator and noted as solvents removed in vacuo. Flash column chromatography (Still et al., *J. Org. Chem.*, 43, 2923 (1978)) was done using Baker grade flash silica gel (47–61 μm) and a silica gel: crude material ratio of about 20:1 to 50:1 unless otherwise stated. Hydrogenation was done at the pressure indicated in the examples or at ambient pressure.

$^1$H-NMR spectra were recorded on a Bruker instrument operating at 300 MHz or 500 MHz and $^{13}$C-NMR spectra were recorded operating at 75 MHz. NMR spectra were obtained as $CDCl_3$ solutions (reported in ppm), using chloroform as the reference standard (7.25 ppm and 77.00 ppm) or $CD_3OD$ (3.4 ppm and 4.8 ppm and 49.3 ppm), or internal tetramethylsilane (0.00 ppm) when appropriate. Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Infrared (IR) spectra were recorded on a Perkin-Elmer FT-IR Spectrometer as neat oils, or as KBr pellets, and when given are reported in wave numbers ($cm^{-1}$). The mass spectra were obtained using LSIMS or electrospray. All melting points (mp) are uncorrected.

The starting materials used in the examples are commercially available and/or can be prepared by techniques known in the art.

EXAMPLE 1

{5-[3-(4,6-Difluoro-1H-benzoimidazol-2-yl)-1H-indazol-5-yl]-4-methyl-pyridin-3-ylmethyl}-ethyl-amine

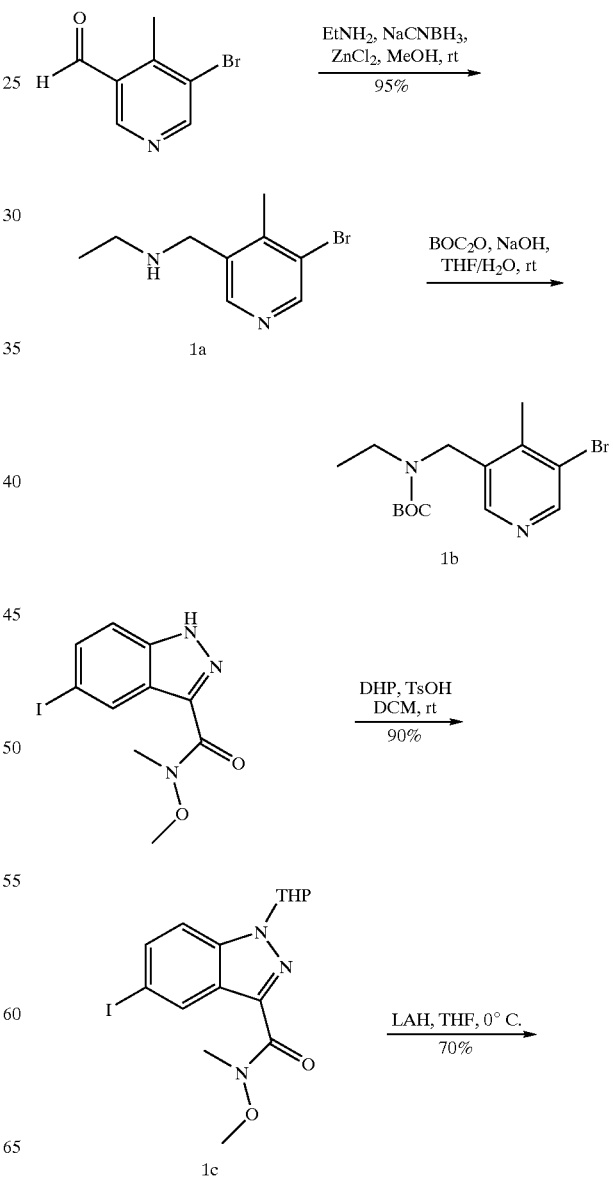

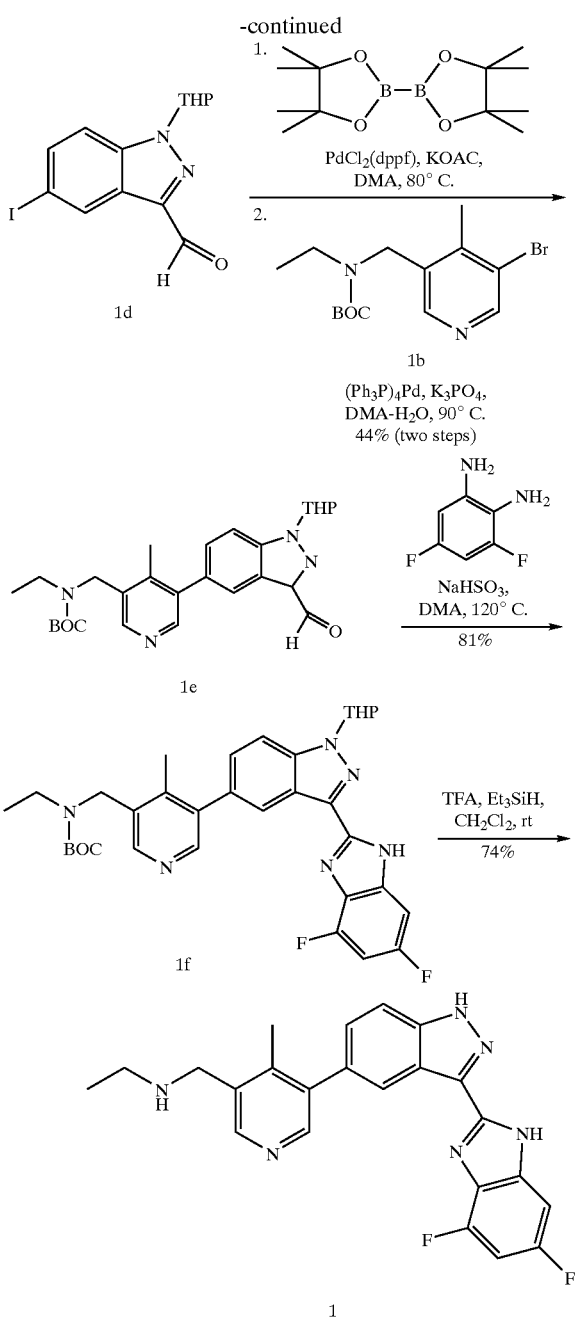

(a) Intermediate 1a—(5-Bromo-4-methyl-pyridin-3-ylmethyl)-ethyl-amine

5-Bromo-4-methyl-pyridine-3-carbaldehyde (6.74 g, 33.7 mmol) [for the preparation of this compound see: Reich, S. R.; Bleckman, T. M.; Kephart, S. E.; Romines, W. H.; Wallace, M. B., U.S. Pat. No. 6,555,539, Apr. 29, 2003.] was dissolved in methanol (290 mL) under a nitrogen atmosphere. A solution of ethylamine in methanol (2.0 M, 90 ml, 180 mmol) was added dropwise over 30 minutes. Stirring was continued at room temperature for 30 minutes further.

In a separate flask, sodium cyanoborohydride (2.33 g, 37.1 mmol) was dissolved in methanol (150 mL). Anhydrous zinc chloride (2.53 g, 18.5 mmol) was added and stirring continued at room temperature for 20 minutes. This solution (zinc/cyanoborohydride) was then slowly added to the above aldehyde/ethylamine solution. The reaction solution was acidified to pH 4 with 2.0 M HCl in methanol (120 mL), and then stirred at room temperature for 18 hours.

The solvents were removed by rotary evaporation and the residue partitioned between ethyl acetate and 10% aqueous sodium carbonate. The organic extracts were dried over magnesium sulfate and concentrated, affording crude amine 1a (7.36 g, 95%) as an orange oil, which was used in the next step without further purification: $^1$H NMR (CDCl$_3$) δ 8.53 (s, 1H), 8.31 (s, 1H), 3.77 (s, 2H), 2.67 (q, J=7.0 Hz, 2 H), 2.42 (s, 3H), 1.11 (t, J=7.0 Hz, 3H).

(b) Intermediate 1b—(5-Bromo-4-methyl-pyridin-3-ylmethyl)-ethyl-carbamic acid tert-butyl ester Di-tert-butyl dicarbonate (10.43 g, 47.8 mmol) was added to a solution of crude amine 1a (7.36 g, 32.1 mmol) in THF (400 mL), followed by aqueous sodium hydroxide solution (1.0 M, 101 mL). The biphasic solution was stirred vigorously for 20 hours at room temperature. The solution was partitioned between water and ethyl acetate; the organic extracts were dried over magnesium sulfate, filtered, and concentrated. The crude yellow oil thus obtained was purified by silica gel chromatography (eluting with a gradient of 10% to 30% ethyl acetate in hexanes), yielded bromopyridine 1b (5.37 g, 51%) as a yellow oil: $^1$H NMR (CDCl$_3$) δ 8.58 (s, 1H), 8.22 (s, 1H), 4.47 (s, 2H), 3.17 (br s, 2H), 2.37 (s, 3H), 1.45 (s, 9H), 1.03 (t, J=7.2 Hz, 3H).

(c) Intermediate 1c—5-Iodo-1-(tetrahydro-pyran-2-yl)-1H-indazole-3-carboxylic acid methoxy-methyl-amide 5-Iodo-1H-indazole-3-carboxylic acid methoxy-methyl-amide [for the preparation of this compound see: Reich, S. R.; Bleckman, T. M.; Kephart, S. E.; Romines, W. H.; Wallace, M. B., U.S. Pat. No. 6,555,539 B2, Apr. 29, 2003.] was alkylated with dihydropyran according to the method of Sun, et. al. [Sun, J.-H.; Teleha, C. A.; Yan, J.-S.; Rogers, J. D.; and Nugiel, D. A., *J. Org. Chem.* 1997, 62, 5627], affording amide 1c (typically >90%) as an off-white powder: $^1$H NMR (DMSO-d$_6$) δ 8.37 (s, 1H), 7.74 (dd, J=1.5, 8.8 Hz, 1H), 7.68 (d, J=8.8 Hz, 1H), 5.97 (dd, J=2.3, 9.0 Hz, 1H), 3.88 (m, 2H), 3.79 (s, 3H), 3.42 (s, 3H), 2.35 (m, 1H), 2.03 (m, 2H), 1.75 (m, 1H), 1.58 (m, 2H).

(d) Intermediate 1d—5-Iodo-1-(tetrahydro-pyran-2-yl)-1H-indazole-3-carbaldehyde

Lithium aluminum hydride (1.2 equiv.) is added portionwise to a cooled (<5° C.) solution of amide 1c (1.0 equiv.) in THF. Stirring is continued at <5° C. until the reaction is complete, typically 30 minutes. The reaction was quenched by the slow addition of ethyl acetate at <5° C., and the whole mixture poured into 0.4 N NaHSO$_4$. The organic layer was washed with brine, dried over magnesium sulfate, concentrated, and purified by silica gel chromatography to give aldehyde 1d (typically ~70%) as an off-white powder: $^1$H NMR (CDCl$_3$) δ 10.15 (s, 1H), 8.47 (s, 1H), 7.82 (dd, J=1.5, 8.7 Hz, 1H), 7.78 (d, J=8.5 Hz, 1H), 6.04 (dd, J=2.3, 9.28 Hz, 1H), 3.85 (m, 2H), 2.35 (m, 1H), 2.05 (m, 2H), 1.76 (m, 1H), 1.60 (m, 2H).

(e) Intermediate 1e—Ethyl-{5-[3-formyl-1-(tetrahydro-pyran-2-yl)-1H-indazol-5-yl]-4-methyl-pyridin-3-ylmethyl}-carbamic acid tert-butyl ester Iodoindazole 1d (3.56 g, 10.0 mmol), bis(pinacolato) diboron (2.79 g, 11 mmol), potassium acetate (2.74 g, 30 mmol) and [1,1'-bis(diphenylphosphino)-ferrocene] dichloropalladium(II)complex with dichloromethane (245 mg, 0.3 mmol) were dissolved in N,N-dimethylacetamide (60 mL). The solution was degassed by evacuating (until the solvent begins to bubble) and purging with Argon (3 cycles), then heated in an 80° C. oilbath for 2 hours. After cooling slightly (to ~50° C.), a solution of bromopyridine 1b (3.62 g, 11 mmol) in N,N-dimethylacetamide (40 mL) was added, followed by deionized water (10 mL) and potassium phosphate (3.18 g, 15 mmol). The solution was degassed, tetrakis(triphenylphosphine) palladium (0) (347 mg, 0.3 mmol) added, and degassed again. The mixture was stirred in a 90° C. oilbath for 4.5 hours. After cooling to room temperature, the mixture was diluted with ethyl acetate (300 mL), washed with deionized water (150 mL), and saturated sodium chloride (100 mL). The organic layer was dried over magnesium sulfate, filtered, and concentrated to a crude red-black oil (9.43 g). Purification by silica gel chromatography (eluting with 50–100% ethyl acetate in hexanes) afforded coupled product 1e (2.9462 g) as an orange oil. $^1$H NMR of this product showed it was contaminated with ~1 equivalent of pinacol. Trituration from hexanes afforded pure 1e (2.0853 g, 44%) as a fine yellow powder: $^1$H NMR (CDCl$_3$) δ 10.25 (s, 1H), 8.39 (s, 1H), 8.34 (s, 1H), 8.22 (s, 1H), 7.74 (d, J=8.7 Hz, 1H), 7.38 (dd, J=1.5, 8.5 Hz, 1H), 5.88 (dd, J=2.8, 9.2 Hz, 1H), 4.53 (s, 2H), 4.03 (m, 1H), 3.81 (m, 1H), 3.24 (br s, 2H), 2.60 (m, 1H), 2.18 (s, 3H), 2.15 (m, 2H), 1.77 (m, 1H), 1.65 (m, 2H), 1.47 (s, 9H), 1.09 (t, J=7.0 Hz, 1H).

(f) Intermediate 1f—{5-[3-(4,6-Difluoro-1H-benzoimidazol-2-yl)-1-(tetrahydro-pyran-2-yl)-1H-indazol-5-yl]-4-methyl-pyridin-3-ylmethyl}-ethyl-carbamic acid tert-butyl ester Aldehyde 1e (2.05 g, 4.28 mmol), 1,2-diamino-3,5-difluorobenzene (617 mg, 4.28 mmol) and sodium bisulfite (891 mg, 8.57 mmol) were dissolved in N,N-dimethylacetamide (43 mL) and heated in a 120° C. oilbath for 21 hours. After cooling to room temperature, the mixture was diluted with ethyl acetate (100 mL) and washed with half-saturated aqueous sodium chloride solution (75 mL, a 1:1 mixture of deionized water and saturated aqueous sodium chloride solution). The aqueous layer was back-extracted with ethyl acetate (2×100 mL). All the organic extracts were combined, dried over magnesium sulfate, and concentrated to a brown tar (3.39 g). This crude material was purified by silica gel chromatography (eluting with a gradient of 70% to 100% ethyl acetate in hexanes), to give benzoimidazole product 1f (2.11 g, 81%) as a tan foam: $^1$H NMR (CD$_3$OD) δ 8.46 (s, 1H), 8.41 (s, 1H), 8.29 (s, 1H), 7.87 (d, J=8.6 Hz, 1H), 7.46 (dd, J=1.3, 8.6 Hz, 1H), 7.13 (m, 1H), 6.84 (m, 1H), 5.99 (dd, J=2.3, 9.9 Hz, 1H), 4.60 (s, 2H), 4.01 (m, 1H), 3.86 (m, 1H), 3.32 (m, 2H, obscured by solvent peak) 2.67 (m, 1H), 2.28 (s, 3H), 2.18 (m, 2H), 1.89 (m, 1H), 1.73 (m, 2H), 1.47 (s, 9H), 1.13 (t, J=7.1 Hz, 1H). Anal. (C$_{33}$H$_{36}$F$_2$N$_6$O$_3$.0.4 H$_2$O) C, H, N, F.

(g) Example 1—{5-[3-(4,6-Difluoro-1H-benzoimidazol-2-yl)-1H-indazol-5-yl]-4-methyl-pyridin-3-ylmethyl}-ethyl-amine Triethyl silane (976 mg, 8.40 mmol) and trifluoroacetic acid (12.9 mL, 168 mmol) were added to a solution of 1f (2.02 g, 3.36 mmol) in dichloromethane (12.9 mL). The mixture was stirred at room temperature for 3.5 hours. The volatiles were removed by rotary evaporation, and the residue treated with cyclohexane (10 mL) and aqueous ammonium hydroxide (2 N, 20 mL). After vigorous stirring for 15 minutes, a pink precipitate forms, which was collected by suction filtration. The filtrate was extracted with ethyl acetate (3×50 mL). The combined organic extracts were dried over magnesium sulfate, filtered, and concentrated to an orange solid (~0.4 g). This solid was added to the pink precipitate obtained above and purified by column chromatography (eluting with a mixture of 1% concentrated ammonium hydroxide to 19% absolute ethanol to 80% dichloromethane). The product thus obtained (1.23 g off-white solid) was further purified by trituration from cyclohexane to yield pure 1 (1.09 g, 74%) as an off-white solid: $^1$H NMR (DMSO-d$_6$) δ 13.81 (very br s, 1H), 8.46 (s, 1H), 8.35 (s, 2H), 7.76 (d, J=8.6 Hz, 1H), 7.44 (dd, J=1.3, 8.6 Hz, 1H), 7.17 (m, 1H), 7.07 (t of d, J$_t$=1.5 Hz, J$_d$=10.6 Hz, 1H) 3.78 (s, 2H), 2.63 (q, J=7.1 Hz, 2H), 2.25 (s, 3H), 1.07 (t, J=7.1 Hz, 3H). HRMS [M+H]$^+$ calc. 419.1791. found 419.1811. Anal. (C$_{23}$H$_{20}$F$_2$N$_6$.1.1 H$_2$O) C, H, N, F.

EXAMPLE 2

Ethyl-{5-[3-(5-fluoro-1H-benzoimidazol-2-yl)-1H-indazol-5-yl]-4-methyl-pyridin-3-ylmethyl}-amine

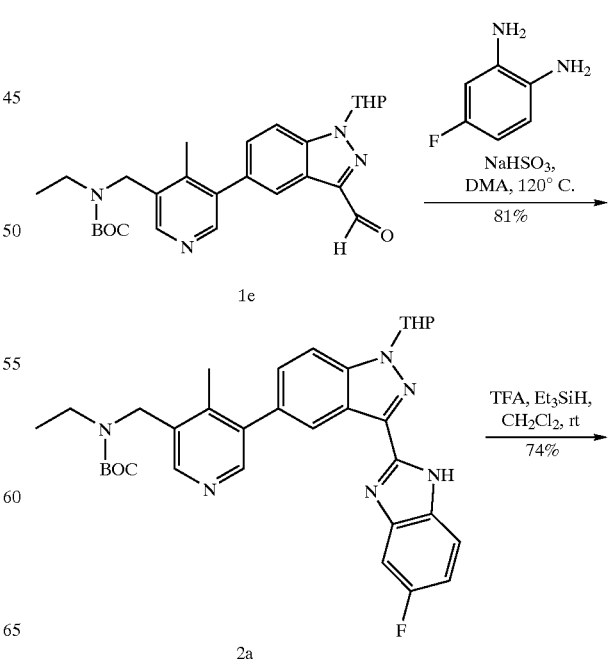

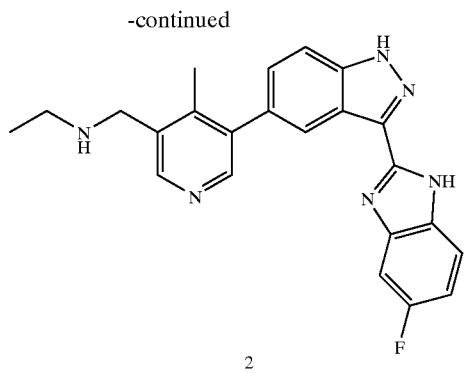

2

(a) Intermediate 2a—Ethyl-{5-[3-(5-fluoro-1H-ben-zoimidazol-2-yl)-1-(tetrahydro-pyran-2-yl)-1H-inda-zol-5-yl]-4-methyl-pyridin-3-ylmethyl}carbamic acid tert-butyl ester By the same procedure used to synthesize intermediate 1f, aldehyde 1e (2.06 g, 4.29 mmol), and 4-fluoro-1,2-phenylenediamine (542 mg, 4.29 mmol) were condensed in the presence of sodium bisulfite (894 mg, 8.59 mmol), affording benzoimidazole 2a (2.04 g, 78%) as an orange foam: $^1$H NMR (DMSO-d$_6$, some peaks are doubled due to tautomeric isomerization) δ 13.15 and 13.13 (2 s, 1H together), 8.42 and 8.41 (2 s, 1H together), 8.39 (s, 1H), 8.32 (s, 1H), 7.77 (dd, J=1.0, 8.9 Hz, 1H), [7.70 (dd, J=4.8, 8.8 Hz) and 7.27 (dd, J=2.5, 9.1 Hz) 1H together], 7.52 (m, 2H), 7.07 (m, 1H), 6.07 (d, J=9.3 Hz 1H), 4.53 (s, 2H), 3.96 (m, 1H), 3.86 (m, 1H), 3.32 (m, 2H) 2.60 (m, 1H), 2.18 (s, 3H), 2.12 (m, 2H), 1.83 (m, 1H), 1.65 (m, 2H), 1.41 (s, 9H), 1.05 (t, J=7.0 Hz, 3H). Anal. ($C_{33}H_{37}FN_6O_3 \cdot 0.5\ H_2O \cdot 0.2$ hexanes) C, H, N, F.

(b) Example 2—Ethyl-{5-[3-(5-fluoro-1H-ben-zoimidazol-2-yl)-1H-indazol-5-yl]-4-methyl-pyridin-3-ylmethyl}-amine In the same manner as the deprotection of 1f, intermediate 2a (1.95 g, 3.34 mmol) was converted to the title compound 2 (1.04 g, 74%), an off white solid: $^1$H NMR (DMSO-d$_6$, some peaks are doubled due to tautomeric isomerization) δ 13.80 (very br s, 1H), 13.12 (very br s, 1H), 8.46 (s, 1H), 8.39 (s, 1H), 8.34 (s, 1H), 7.69 and 7.25 (2 m, 1H together), 7.48 (m, 1H), 7.44 (dd, J=1.5, 8.6 Hz, 1H), 7.05 (m, 1H), 3.77 (s, 2H), 2.62 (q, J=7.3 Hz, 2H), 2.25 (s, 3H), 1.07 (t, J=7.1 Hz, 3H). Anal. ($C_{23}H_{21}FN_6 \cdot 1.1\ H_2O$) C, H, N, F.

Biochemical and Biological Evaluation

Cyclin-dependent kinase activity was measured by quantifying the enzyme-catalyzed, time-dependent incorporation of radioactive phosphate from [$^{32}$P]ATP or [$^{33}$P]ATP into a protein substrate. Unless noted otherwise, assays were performed in 96-well plates in a total volume of 50 μL, in the presence of 10 mM HEPES (N-[2-hydroxyethyl]piperazine-N'-[2-ethanesulfonic acid]) (pH 7.4), 10 mM MgCl$_2$, 25 μM adenosine triphosphate (ATP), 1 mg/mL ovalbumin, 5 μg/mL leupeptin, 1 mM dithiothreitol, 10 mM beta-glycerophosphate, 0.1 mM sodium vanadate, 1 mM sodium fluoride, 2.5 mM ethylene glycol-bis(β-aminoethyl ethKer)-N,N,N'N'-tetraacetic acid (EGTA), 2% (v/v) dimethylsulfoxide, and 0.03–0.4 μCi [$^{32/33}$P]ATP per reaction. Reactions were initiated with enzyme, incubated at 30° C., and terminated after 20 minutes by the addition of ethylenediaminetetraacetic acid (EDTA) to 250 mM. The phosphorylated substrate was then captured on a nitrocellulose or phosphocellulose membrane using a 96-well filtration manifold, and unincorporated radioactivity was removed by repeated washing with 0.85% phosphoric acid. Radioactivity was quantified by exposing the dried membranes to a phosphorimager.

Apparent $K_i$ values were measured by assaying enzyme activity in the presence of different inhibitor compound concentrations and subtracting the background radioactivity measured in the absence of enzyme. Inhibition data were fit to an equation for competitive inhibition using Kaleidagraph (Synergy Software), or were fit to an equation for competitive tight-binding inhibition using the software KineTic (BioKin, Ltd.).

Inhibition of CDK4/Cyclin D Retinoblastoma Kinase Activity

A complex of human CDK4 and cyclin D3, or a complex of human CDK4 and genetically truncated (1–264) cyclin D3, was purified using traditional biochemical chromatographic techniques from insect cells that had been co-infected with the corresponding baculovirus expression vectors (see e.g., Meijer and Kim, "Chemical Inhibitors of Cyclin-Dependent Kinases," Methods in Enzymol. vol. 283 (1997), pp. 113–128.). The enzyme complex (5 or 50 nM) was assayed with 0.3–0.5 μg of purified recombinant retinoblastoma protein fragment (Rb) as a substrate. The engineered Rb fragment (residues 386–928 of the native retinoblastoma protein; 62.3 kDa) contains the majority of the phosphorylation sites found in the native 106-kDa protein, as well as a tag of six histidine residues for ease of purification. Phosphorylated Rb substrate was captured by microfiltration on a nitrocellulose membrane and quantified using a phosphorimager as described above. For measurement of tight-binding inhibitors, the enzyme complex concentration was lowered to 5 nM, and the assay duration was extended to 60 minutes, during which the time-dependence of product formation was linear.

Inhibition of CDK2/Cyclin A Retinoblastoma Kinase Activity

CDK2 was purified using published methodology (Rosenblatt et al., "Purification and Crystallization of Human Cyclin-dependent Kinase 2," J. Mol. Biol., vol. 230, 1993, pp. 1317–1319) from insect cells that had been infected with a baculovirus expression vector. Cyclin A was purified from E. coli cells expressing full-length recombinant cyclin A, and a truncated cyclin A construct was generated by limited proteolysis and purified as described previously (Jeffrey et al., "Mechanism of CDK activation revealed by the structure of a cyclin A-CDK2 complex," Nature, vol. 376 (27 Jul. 1995), pp. 313–320). A complex of CDK2 and proteolyzed cyclin A was prepared and purified by gel filtration. The substrate for this assay was the same Rb substrate fragment used for the CDK4 assays, and the methodology of the CDK2/cyclin A and the CDK4/cyclin D3 assays was essentially the same, except that CDK2 was present at 150 nM or 5 nM. $K_i$ values were measured as described above.

The stimulation of cell proliferation by growth factors such as VEGF and others is dependent upon their induction of autophosphorylation of each of their respective receptor's tyrosine kinases. Therefore, the ability of a protein kinase inhibitor to block cellular proliferation induced by these growth factors is directly correlated with its ability to block receptor autophosphorylation. To measure the protein kinase inhibition activity of the compounds, the following constructs were used.

Inhibition of Cell Growth: Assessment of Cytotoxicity

Inhibition of cell growth was measured using the tetrazolium salt assay, which is based on the ability of viable cells to reduce 3-(4,5-dimethylthiazol-2-yl)-2,5-[2H]-diphenyltetrazolium bromide (MTT) to formazan (Mossman, Journal of Immunological Methods, vol. 65 (1983), pp. 55–58). The water-insoluble purple formazan product was then detected spectrophotometrically. The HCT 116 cell line was grown in 96-well plates. Cells were plated in the appropriate medium at a volume of 135 μl/well in McCoy's 5A Medium. Plates were incubated for four hours before addition of inhibitor compounds. Different concentrations of inhibitor compounds were added in 0.5% (v/v) dimethylsulfoxide (15 μL/well), and cells were incubated at 37° C. (5% $CO_2$) for four to six days (depending on cell type). At the end of the incubation, MTT was added to a final concentration of 0.2 mg/mL, and cells were incubated for 4 hours more at 37° C. After centrifugation of the plates and removal of medium, the absorbance of the formazan (solubilized in dimethylsulfoxide) was measured at 540 nm. The concentration of inhibitor compound causing 50% inhibition of growth was determined from the linear portion of a semi-log plot of inhibitor concentration versus percentage inhibition. All results were compared to control cells treated only with 0.5% (v/v) dimethylsulfoxide.

Panel of Protein Kinases

The compounds of the present invention were screened against a large panel of protein kinase to determine inhibition activity for CDK as against a variety of protein kinases. The assay was conducted using methods and materials described by Davies, S et al. *Specificity and Mechanism of Action of Some Commonly Used Protein Kinase Inhibitors*, Biochem J. 351, 95–105 (2000), the contents of which are herein incorporated by reference. The compounds were screened against a panel of protein kinases which include AMP-activiated protein kinase (AMPK), checkpoint kinase (CHK1), casein kinases 1 and 2 (CK1 and CK2), cytoplasmic tyrosine kinase (CSK), dual serine/threonine/tyrosine kinase (DYRK1A), glycogen synthase kinase 3 (GSK3B), c-Jun N-terminal kinase (JNK), lymphocyte kinase (LCK), mitogen-activated protein kinases 2, K-1a, K2 (MAPK2, MAPKAP-K1a, and MAPKAP-K2), MAPK kinase (MKK1, also called MEK), mitogen and stress-activated protein kinase 1 (MSK1), never-in-mitosis kinase 6 (NEK6), p70 ribosomal protein S6 kinase (P70s6K1), 3-phosphoinositide-dependent protein kinase 1 (PDK1), phosphorylase kinase (PHK), protein kinase A (PKA), protein kinase B (PKB, also called Akt), protein kinase C (PKCa), p38-regulated/activated kinase (PRAK), Rho-dependent protein kinase (ROCK-II), stress-activated protein kinase 2a, 2b, 3 and 4 (SAPK-2A or p38, SAPK-2b or p38β2, SAPK3 or p38γ, SAPK4 or p38δ, respectively), and serum- and glucocorticoid-induced kinase (SGK). Compound activity was grouped into categories of weak (<50%), moderate (50–75%) and strong inhibition (>75%). As illustrated by Table 1 below, the compounds of the present invention are potent CDK inhibitors and are unexpectedly more selective for CDK inhibitors as compared to 3,5 substituted indazoles taken from U.S. Pat. No. 6,555,539.

TABLE 1

| Kinase Activity of 3,5 Indazole Compounds | | | | | | |
|---|---|---|---|---|---|---|
| | A* | B* | C* | D* | 1 | 2 |
| CDK2/A $K_i$ (nM) | 0.52 | 0.25 | 0.80 | 2.40 | 0.78 | 0.47 |
| HCT-116 $IC_{50}$ (nM) | 70 | 90 | 86 | >500 | 120 | 22 |
| Kinase | | | | | | |
| AMPK | ++ | ++ | ++ | ++ | ++ | ++ |
| CDK2/A | ++ | ++ | ++ | ++ | ++ | ++ |
| CHK1 | + | + | − | − | − | − |
| CK1 | − | − | − | − | − | − |
| CK2 | − | − | − | − | − | − |
| CSK | − | − | − | − | − | − |
| DYRK1A | ++ | ++ | ++ | ++ | ++ | ++ |
| GSK3B | ++ | ++ | ++ | ++ | ++ | ++ |
| JNK | − | − | − | − | − | − |
| LCK | ++ | ++ | + | − | + | + |
| MAPK2 | − | − | − | − | − | − |
| MAPKAP-K1a | ++ | ++ | ++ | + | ++ | − |
| MAPKAP-K2 | − | − | − | − | − | − |
| MKK1 | ++ | + | + | + | − | − |
| MSK1 | − | − | − | − | − | − |
| NEK6 | − | − | − | − | − | − |
| P70s6K1 | + | + | − | − | − | − |
| PDK1 | + | − | − | − | − | − |
| PHK | ++ | + | + | − | + | ++ |
| PKA | ++ | ++ | + | − | − | − |
| PKB | − | − | − | − | − | − |
| PKCa | + | ++ | + | − | − | − |
| PRAK | ++ | + | ++ | + | − | − |
| ROCK-II | ++ | + | + | − | − | + |
| SAPK-2A | − | − | − | − | − | − |
| SAPK-2b | − | − | − | − | − | − |
| SAPK3 | − | − | − | − | − | − |
| SAPK4 | − | − | − | − | − | − |
| SGK | + | + | − | − | − | − |

++ Strong inhibition >75%
+ Moderate inhibition 50–75%
− Weak inhibition <50%
*Compounds A, B, C and D are described in U.S. Pat. No. 6,555,539.

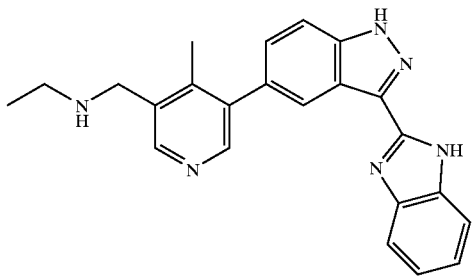

A

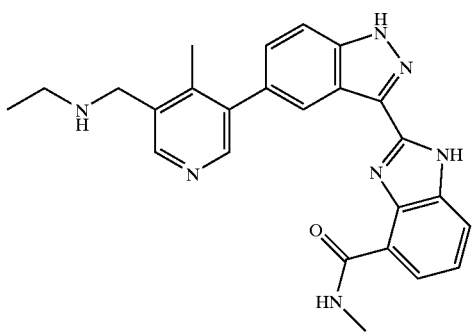

B

C

TABLE 1-continued

Kinase Activity of 3,5 Indazole Compounds

| A* | B* | C* | D* | 1 | 2 |
|---|---|---|---|---|---|

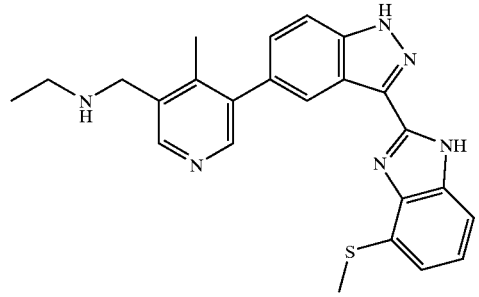

D

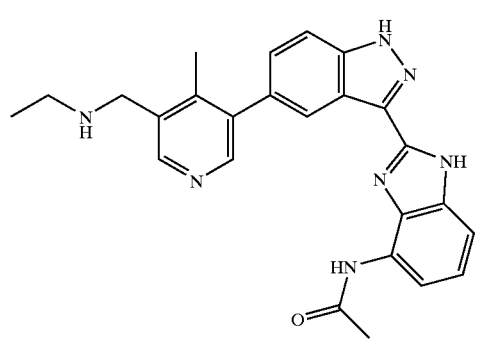

1

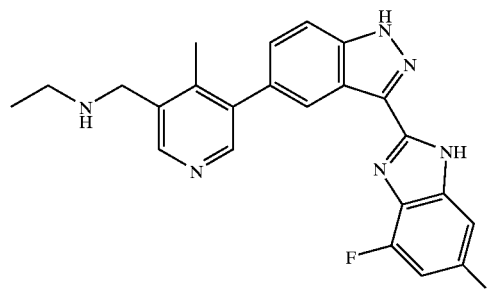

2

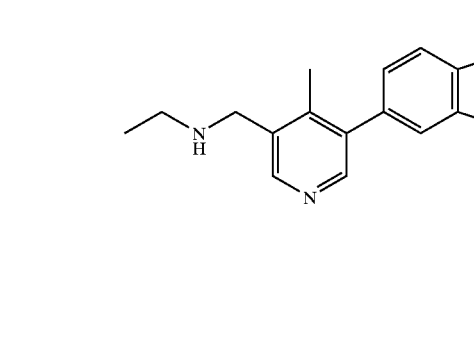

Additional assays may readily be performed to determine the selectivity of compounds of Formula I for CDK against other kinase complexes, i.e. VEGF or FGFR (fibroblast growth factor receptor) kinases. Such assays are described in U.S. Pat. No. 6,555,539 and WO 03/004488 and are known in the art.

The exemplary compounds described above may be formulated into pharmaceutical compositions according to the following general examples.

Parenteral Composition

To prepare a parenteral pharmaceutical composition suitable for administration by injection, 100 mg of a water-soluble salt of a compound of Formula I is dissolved in DMSO and then mixed with 10 mL of 0.9% sterile saline. The mixture is incorporated into a dosage unit form suitable for administration by injection.

Oral Composition

To prepare a pharmaceutical composition for oral delivery, 100 mg of a compound of Formula I is mixed with 750 mg of lactose. The mixture is incorporated into an oral dosage unit for, such as a hard gelatin capsule, which is suitable for oral administration.

While the invention has been illustrated by reference to specific and preferred embodiments, those skilled in the art will recognize that variations and modifications may be made through routine experimentation and practice of the invention. Thus, the invention is intended not to be limited by the foregoing description, but to be defined by the appended claims and their equivalents.

The invention claimed is:

1. A compound of the formula

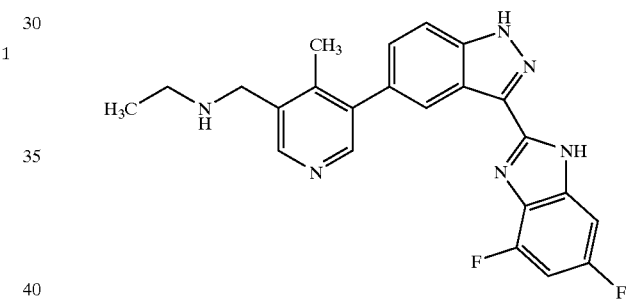

or a pharmaceutically acceptable salt thereof.

2. A pharmaceutical composition comprising a compound according to claim 1.

3. A compound of the formula

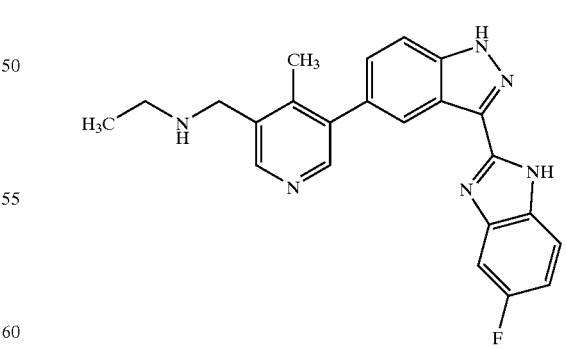

or a pharmaceutically acceptable salt thereof.

4. A pharmaceutical composition comprising a compound according to claim 2.

* * * * *